US007300755B1

(12) United States Patent
Petersdorf et al.

(10) Patent No.: US 7,300,755 B1
(45) Date of Patent: Nov. 27, 2007

(54) METHODS FOR HAPLOTYPING GENOMIC DNA

(75) Inventors: Effie W. Petersdorf, Seattle, WA (US); Zhen Guo, Bellevue, WA (US); Leroy Hood, Seattle, WA (US)

(73) Assignees: Fred Hutchinson Cancer Research Center, Seattle, WA (US); Institute for Systems Biology, Seattle, WA (US)

( * ) Notice: Subject to any disclaimer, the term of this patent is extended or adjusted under 35 U.S.C. 154(b) by 362 days.

(21) Appl. No.: 10/843,985

(22) Filed: May 12, 2004

Related U.S. Application Data

(60) Provisional application No. 60/470,322, filed on May 12, 2003.

(51) Int. Cl.
*C12Q 1/68* (2006.01)
*C07H 21/02* (2006.01)
*C07H 21/04* (2006.01)
(52) U.S. Cl. .................. 435/6; 536/23.1; 536/24.3
(58) Field of Classification Search .................. 435/6; 536/23.1, 24.3
See application file for complete search history.

(56) References Cited

U.S. PATENT DOCUMENTS

| | | | | |
|---|---|---|---|---|
| 4,401,796 A | | 8/1983 | Itakura | 525/340 |
| 4,458,066 A | | 7/1984 | Carruthers | 536/25.34 |
| 4,500,707 A | | 2/1985 | Carruthers | 536/25.34 |
| 4,582,788 A | | 4/1986 | Erlich | 435/6 |
| 4,835,098 A | | 5/1989 | Orr et al. | 435/6 |
| 5,175,082 A | * | 12/1992 | Jeffreys | 435/6 |
| 5,468,613 A | * | 11/1995 | Erlich et al. | 435/6 |
| 5,482,836 A | * | 1/1996 | Cantor et al. | 435/6 |
| 5,629,149 A | | 5/1997 | Santamaria et al. | 435/6 |
| 5,759,778 A | * | 6/1998 | Li et al. | 435/6 |
| 5,851,769 A | * | 12/1998 | Gray et al. | 435/6 |
| 5,972,604 A | | 10/1999 | Santamaria et al. | 435/6 |
| 6,268,133 B1 | * | 7/2001 | Nisson et al. | 435/6 |
| 6,306,643 B1 | | 10/2001 | Gentalen et al. | 435/6 |
| 6,638,717 B2 | * | 10/2003 | Perrin et al. | 435/6 |
| 6,844,154 B2 | | 1/2005 | Landers | 435/6 |
| 2004/0185453 A1 | * | 9/2004 | Myerson et al. | 435/6 |
| 2006/0046251 A1 | * | 3/2006 | Sampson et al. | 435/6 |

FOREIGN PATENT DOCUMENTS

WO    WO 00/79006 A1    12/2000

OTHER PUBLICATIONS

Ito et al., Sequence-specific DNQA purification by triple helix affinity capture. PNAS 89 : 495-498 (1992).*
Guo et al., Long-range multilocus haplotype phasing of the MHC. PNAS 103 (18) :6964-6969 (1996).*
Guo et al., Oligonucleortide arrays for High -throughput SNPs detecton in the MHC Class I genes : HLA-B as a model system. Genome Research 12: 447-457 (2001).*
Kandpal et al. Selective enrichment of a large size genomic DNA fragment by affinity capture : an approach for genome mapping. Nucleic Acids Research 18 (7) : 1789-1795.*
Guo et al., Oligonucleotide arrays for high resolution HLA typing. Reviews in Immunogenetics 1:220-230 (1999).*
Ryskov et al. Purification of large DNA fragments enriched in globin gene sequences 3: 81-85 (1978).*
Kim et al., Solid-phase genetic engineerinbg with DNA immobilized on a gold surface. J. of Biotechnology 96: 213-221 (2002).*
Kandpal et al., Chromosome Fishing : An affinity capture method for selective enrichment of Large genomic DNA fragments. Methods in Enzymology 216 : 39-54 (1992).*
Gou et al.; "Long-range multilocus haplotype of the MHC" *Proc. Natl. Acad. Sci.* 103:6964-6969 (2006).
Gou et al.; Online Supporting Information for: "Long-range multilocus haplotype phasing of the MHC" *Proc. Natl. Acad. Sci.* 103:6964-6969 (2006).
Flomenberg et al.; "Impact of HLA class I and class II high-resolution matching on outcomes of unrelated donor bone marrow transplatation: HLA-C mismatching is associated with a strong adverse effect on transplantation outcome" *Blood* 104(7):1923-1930 (2004).
Gentalen et al.; "A novel method for determining linkage between DNA sequences: hybridization to paired probe arrays" *Nucleic Acids Research* 27(6):1485-1491 (1999).
The MHC Sequencing Consortium; "Complete sequence and gene map of a human major histocompatibility complex" *Nature* 401:921-923 (1999).
Gou et al.; "Enhanced discrimination of single nucleotide polymorphisms by artificial mismatch hybridization" *Nature Biotech* 15:331-335 (1997).

(Continued)

*Primary Examiner*—Ethan Whisenant
(74) *Attorney, Agent, or Firm*—Myers Bigel Sibley & Sajovec, P.A.

(57) ABSTRACT

The present invention provides a novel method for specifically isolating and separating large segments of genomic DNA that can subsequently be used to determine a genomic haplotype. The invention relies on using a solid phase having a flat surface arrayed with oligonucleotides designed to specifically hybridize to each particular haplotype of an individual sample, e.g., oligonucleotides designed to specifically hybridize with each of the two HLA-B haplotypes, HLA-A, HLA-C, HLA-DR, HLA-DQ, and the like. The genomic DNA is contacted and hybridized to the arrayed oligonucleotides to form a genomic DNA/oligonucleotide complex. The excess genomic DNA is washed away and the haplotype separated genomic DNA is denatured from the oligonucleotide probe and collected. The method of the present invention allows for the separation of genomic DNA fragments of between approximately 2 to about 4 megabases (Mb). Separation of the haplotypes of large genomic DNA fragments allows for linkage analysis of other HLA alleles and polymorphisms, microsatellite, SNPs, and the like across a large span of the HLA region, including HLA-A, -B, -C, and HLA-DRB1 regions. This linkage analysis is particularly useful when HLA typing for an individual with limited family HLA typing available.

15 Claims, No Drawings

OTHER PUBLICATIONS

Fernandez-Vina et al.; "Population diversity of B-locus alleles observed by high-resolution DNA typing" *Tissue Antigens* 45(3):153-168 (1995). *Abstract only.*

Petersdorf et al.; "A comprehensive approach for typing the alleles of the HLA-B locus by automated sequencing" *Tissue Antigens* 46:73-85 (1995).

Gou et al.; "Direct fluorescence analysis of genetic polymorphisms by hybridization with oligonucleotide arrays on glass supports" *Nucl Acids Res* 22(24):5456-5465 (1994).

U.S. Appl. No. 10/081,112, filed Oct. 28, 2002, Petersdorf et al.

U.S. Appl. No. 11/517,956, filed Sep. 7, 2006, Petersdorf et al.

Begovich et al.; "Polymorphism, recombination, and linkage disequilibrium within the HLA class II region" *J. Immunology* 148(1):249-258 (1992).

Maskos et al.; "Oligonucleotide hybridisations on glass supports: a novel linker for oligonucleotide synthesis and hybridisation proerties of oligonucleotides synthesised in situ" *Nucl Acids Res* 20(7):1679-1684 (1992).

Bjorkman et al.; "Structure of the human class I histocompatibility antigen, HLA-A2" *Nature* 329(8):506-512 (1987).

* cited by examiner

METHODS FOR HAPLOTYPING GENOMIC DNA

CROSS-REFERENCES TO RELATED APPLICATIONS

This application claims the benefit of U.S. Provisional Patent Application No. 60/470,322, filed on May 12, 2003, which is incorporated herein by reference in its entirety.

STATEMENT AS TO RIGHTS TO INVENTIONS MADE UNDER FEDERALLY SPONSORED RESEARCH AND DEVELOPMENT

The present invention was developed in part with government support under grant numbers CA72978 and CA15704 awarded by the National Cancer Institute of the National Institutes of Health. The government has certain rights in this invention.

FIELD OF THE INVENTION

The present invention provides a method for specifically isolating and separating large segments of genomic DNA that can be subsequently used to determine genomic haplotypes.

BACKGROUND OF THE INVENTION

The major histocompatibility complex (MHC) is the most comprehensively studied multi-megabase region of the human genome, motivated by the biomedical importance of the HLA and resident genes. More than 224 genes have now been identified within the 3,673,800 bases of the MHC (The MHC Sequencing Consortium, Nature 401:921-923, 1999), an estimated 40% of which are involved in immune function. The classical transplatation genes, HLA-A, -B, and -C in the class I region and HLA-DR, -DQ, and -DP in the class II region, share structural properties and encode polypeptides that are critical in controlling T cell recognition and determining histocompatibility in transplantation (Bjorkman et al., Nature 329:506-512, 1987). The class II region contains at least 7 genes involved in inflammation (Gruen and Weissman, Blood 90:4252-4265, 1997). The clustering of genes that share similar function within the MHC is striking and unlikely to be coincidental (Bjorkman et al., Nature 329:506-512, 1987; Rammensee, Curr. Opin. Immunol. 7:85-96, 1995). The class II region is noteworthy as most are immune-related genes whose functions include loading and assembly of class II gene products (DM), peptide editing (DN/DO), transport of cytosolic proteins for presentation by class I (TAP in association with calnexin, calreticulin, tapasin, Erp57 protein) and proteosome degradation genes (LMP)(Beck et al., J. Mol. Biol. 228:433-441, 1992).

A hallmark of HLA genes is their extensive degree of polymorphism, driven by selection of alleles for protection against environmental insult and infection (Bodmer, Nature 237:139-145, 1972). Nucleotide substitutions that distinguish unique alleles and allele families are not random; HLA allele diversity is characterized by substitutions that affect peptide binding repertoire and contact to the T cell receptor. Extensive variation is not confined to coding sequences of HLA genes. Variation in non-coding regions flank the highly polymorphic HLA genes (Horton et al., J. Mol. Biol. 282: 71-97, 1998), possibly as the result of over-dominant allele selection (Maynard-Smith and Haigh, Genet. Res. 23:23-27, 1974). Diversityin promoter gene sequences mayconfer important effects on gene expression (Trowsdale, in: HLA and MHC: Genes, Molecules, and Function, Browning and McMichael, eds., BIOS Scientific Publishers, Oxford, UK, p. 22, 1996).

A hallmark of HLA genes is their extensive degree of polymorphism, driven by selection of alleles for protection against environmental insult and infection (Bodmer, Nature 237:139-145, 1972). Nucleotide substitutions that distinguish unique alleles and allele families are not random; HLA allele diversity is characterized by substitutions that affect peptide binding repertoire and contact to the T cell receptor. Extensive variation is not confined to coding sequences of HLA genes. Variation in non-coding regions flank the highly polymorphic HLA genes (Horton et al., J. Mol. Biol. 282: 71-97, 1998), possibly as the result of over-dominant allele selection (Maynard-Smith and Haigh, Genet. Res. 23:23-27, 1974). Diversity in promoter gene sequences may confer important effects on gene expression (Trowsdale in, HLA and MHC: Genes, Molecules, and Function, Browing and MiMichael eds., BIOS Publishers, Oxford, UK. p. 22, 1996).

A unique feature of the MHC is the high degree of non-random association of alleles at two or more HLA loci, a phenomenon termed linkage disequilibrium (LD). LD is thought to represent an evolutionary advantage in the face of genetic randomizing pressures of mutation, recombination, selection and genetic drift. The arrangement of certain MHC alleles together on a haplotype is hypothesized to permit matching of variation in cis and possibly confer survival advantage to the organism (Santamaria, et al., Human Immunol. 37:39-50, 1993). Traditionally, HLA haplotypes are determined by typing as many members of a family as are available in order to establish the gametic assignment. In the absence of family study, haplotype frequencies can be estimated (Begovich et al., J. Immunol. 148:249-258, 1992; Ceppellini et al., in, HLA Testing 1967, Copenhagen, Munksgaard, p. 149, 1967). For example, among individuals with the HLA-A1,2; B7,8; DR2,3 phenotype, the 4 possible 3-locus haplotypes are: HLA-A1, B8, DR3 with A2, B7, DR2; A1, B8, DR2 with A2, B7, DR3; A2, B8, DR3 with A1, B7, DR2; and A2, B8, DR2 with A1, B7, DR3. Linkage disequilibria estimates predict A1, B8, DR3 and A2, B7, DR2 to be the likely haplotypes in this example.

The most well known and studied haplotype, HLA-A1, -B8, -DR3, demonstrates conservation of HLA and non-HLA markers to almost 90% in the Australian Caucasoid population (Piazza, Histocompatability Testing 1975, Copenhagen, Munksgaard, p. 923, 1975). The effect of the A1, B8, DR3 haplotype on both humoral and cellular immunity has been demonstrated: T-cell and NK cell numbers; IL-2, -4, -5, -6 production; IFN-γ production; CD69 and CD71 expression; macrophage function; Fas expression; Fas-induced apoptosis; antibody production as measured by response to vaccines; IgE response, and titers of autoantibodies. The A1, B8, DR3 haplotype is best studied as a disease susceptibility determinant for type 1 diabetes, pemphigus vulgaris, myasthenia gravis, systemic lupus erythematosis, scleroderma, celiac disease and HIV progression. More generally, HLA haplotypes are known to influence responsiveness to vaccines (Clayton and Lonjou, HLA 1:665-829, 1997; Price et al., Immunol. Rev. 167:257-274, 1999; Mitchell et al., J. Clin. One. 10:1158-1164, 1992), are informative for analysis of anthropologic and evolutionary studies (Egea et al., J. Exp. Med. 173:531-538, 1991; Hatae et al., Euro. J. Immunol. 22:1899-1905, 1992; Lewontin, Evol. Biol. 6:381-398, 1972; Piazza et al., Proc. Natl. Acad. Sci. USA 78:2638-2642, 1981; Klitz et al., Human Genet.

39:340-349, 1986; Hughes and Nei, *Nature* 335:167-170, 1988; Serjeantson, in, *The colonization of the Pacific: A Genetic Trial*, Hill and Serjeantson eds., Oxford University Press, New York, pp. 120-135, 1989; Klein, *Human Immunol.* 19:155-162, 1987; Trowsdale, *Immunogenetics* 41:1-17, 1995), as well as in forensic medicine (Bergstrom et al., *Am. J. Human Genet.* 64:1709-1718, 1999). In the field of transplantation, estimated haplotype frequencies have been used to facilitate allocation of solid organs (Gonser et al., *Genetics* 154:1793-1807, 2000; Terasaki et al., *Forensic Sci. Intern.* 12:227, 1978; Takemoto et al., *N. Engl. J. Med.* 331:760, 1994; Zachary et al., *Transplantation* 62:272-283, 1996) and determine the ideal size of unrelated donor registries for stem cell transplantation (Kriett and Kaye, *J. Heart Lung Tranplant.* 10:491, 1991; Takahashi et al., *Transfusion* 29:311-316, 1989; Beatty et al., *Tranplantation* 60: 778-783, 1995; Schipper et al., *Human Immunol.* 52:54-71, 1997).

There is widespread utility in establishing the association of markers regardless of the chromosome under study. Traditionally, pedigree analysis has been used to determine the linkage within a family. Without a family study the degree of linkage disequilibrium can be estimated (NIH/CEPH Collaborative Mapping Group, *Science* 258:67-86, 1992). The lack of family members of unrelated stem cell donors to ascertain the donor's haplotypes has required search strategies to rely on typing and matching each individual HLA gene. What is needed in the art is a method for determining the two extended HLA haplotypes in individuals lacking a family study.

BRIEF SUMMARY OF THE INVENTION

The present invention provides a method for separating large fragments of genomic DNA by haplotype, comprising (a) providing a flat solid surface comprising a covalently bound oligonucleotide probe having a nucleotide sequence complementary to a plurality of haplotypes of a HLA locus; (b) contacting the bound oligonucleotide probes with a sample of genomic DNA under conditions conducive to specific hybridization of the genomic DNA to the plurality of oligonucleotide probes to form a genomic DNA/oligonucleotide complex; (c) removing excess genomic DNA; (d) denaturing the genomic DNA/oligonucleotide complex; and (e) separating the genomic DNA by haplotype. In a particular embodiment of the invention probes are designed to specifically separate the genomic DNA by two haplotypes of the HLA-B locus. Typically the oligonucleotide probe is about 20 to about 40 bases in length. The oligonucleotide probes are spaced on the surface of the solid phase to allow independent manipulation of the genomic DNA hybridized to each probes. In a particular embodiment the hybridization is carried out at room temperature overnight.

In another embodiment of the present invention a method for determining cis linkage of HLA alleles to an HLA locus haplotype, is provided. The method comprises (a) providing a flat solid surface comprising a covalently bound plurality of oligonucleotide probes having a nucleotide sequence complementary to a HLA locus haplotype; (b) contacting the oligonucleotide probe with a sample of genomic DNA under conditions conducive to specific hybridization of the genomic DNA to the oligonucleotide probe to form a genomic DNA/oligonucleotide complex; (c) removing excess genomic DNA; (d) denaturing the genomic DNA/oligonucleotide complex; (e) separating the genomic DNA by haplotype; (f) amplifying selectively an HLA region in the haplotype separated genomic DNA using asymmetric PCR and labeled primers to form a labeled, single stranded DNA sample; (g) contacting the labeled, single stranded DNA sample with a microarray comprising a plurality of HLA oligonucleotide probes under conditions conducive to hybridization; and (i) detecting a hybridization pattern for the DNA sample and assigning the HLA allele type with cis linkage to the HLA locus haplotype of the genomic DNA sample. In a particular embodiment of this aspect of the invention the plurality of oligonucleotide probes is selected to be specific for the haplotypes of the HLA-B locus. The linkage of polymorphisms in the HLA-A, -C, -DR and -DQ regions can be determined by the designing of, and using probes known to distinguish alleles and polymorphisms in these regions.

The present invention also provides a method for HLA tissue typing. The method comprises (a) separating a genomic DNA sample into a first and a second HLA-B locus haplotype; (b) amplifying exons 2 and 3 from the haplotype separated DNA sample using labeled primers and an asymmetric PCR method to form a labeled, single-stranded DNA sample; (c) contacting the labeled, single-stranded DNA sample under hybridization conditions with an array of HLA oligonucleotide probes; and (d) detecting a hybridization pattern for the DNA sample and assigning an HLA allele type by analysis of the hybridization pattern with the first and second HLA-B locus haplotypes.

DETAILED DESCRIPTION OF THE INVENTION

The present invention provides a method for separating large genomic DNA segments or fragments by haplotype. The haplotype separated genomic fragments can be used to determine the extended HLA haplotypes in individuals, such as those lacking a family HLA typing study. The method can use either serological or DNA HLA typing information for the sample to identify the cis/trans association of alleles with an HLA locus. The method provides for specifically isolating and separating large segments of genomic DNA of about 2 to about 4 megabases that can be subsequently used to determine genomic haplotypes. The method relies on using a solid phase, such as a flat glass slide, arrayed with oligonucleotides designed to specifically hybridize to a specific haplotype of an individual sample. The genomic DNA is exposed and hybridized to the arrayed oligonucleotides under conditions conducive to hybridization and the genomic DNA is separately released from the surface of the array.

The array format is ideally suited for this application because the method requires a solid-phase format, the separation of the two HLA haplotypes is based on differences in the primary nucleotide sequences of the haplotype, and the methods must be efficient for large-scale population analysis. The method provides for the attachment of an oligonucleotide probe which can specifically hybridize to one or the other haplotype of a known gene or locus, such as, the HLA-A, -B, C, -DR, -DQ, or -DR genes. The separation of HLA haplotypes is based on discrimination of differences between the primary nucleotide sequences of the haplotypes, and not on size, as the two haplotypes have identical or similar basepair lengths.

HLA-B is an ideal locus to separate the two extended haplotypes as the location of the gene within the MHC assures the template will span the region of the genomic DNA that comprises from HLA-DQ through HLA-A at a minimum. Furthermore, the use of HLA-B as the point of separation provides unambiguous hybridization patterns regardless of the combination of alleles. In the first step, two probes which can specifically separate the HLA-B haplotypes, e.g., a each probe having a length of about 20 to about 40, or more nucleotides, are selected. The probes are generally covalently attached to the solid support using a linking group that is sufficient to provide optimum binding of a sample nucleic acid to the probe array. The probes are arrayed to allow separate manipulation of each spot on the solid phase surface. Genomic DNA is allowed to hybridize to the probe on the surface of the solid phase; the DNA from one haplotype hybridizing only to the first probe that shares complementarity in sequence and any DNA from the second haplotype hybridizing to the second probe. Excess genomic DNA is eliminated with a buffer wash. The haplotyped DNA from each probe can be separately released by denaturing the hybridized probe/DNA complex and removing the DNA.

As used herein, the term "nucleic acid" or "oligonucleotide" refers to a deoxyribonucleotide or ribonucleotide in either single- or double-stranded form. The term also encompasses nucleic-acid-like structures with synthetic backbones. DNA backbone analogues provided by the invention include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see *Oligonucleotides and Analogues, a Practical Approach*, edited by F. Eckstein, IRL Press at Oxford University Press (1991); "Antisense Strategies", *Annals of the New York Academy of Sciences, Volume 600*, Eds. Baserga and Denhardt (NYAS 1992); Milligan, *J. Med. Chem.* 36:1923-1937, 1993; *Antisense Research and Applications* (1993, CRC Press). PNAs contain non-ionic backbones, such as N-(2-aminoethyl)glycine units. Phosphorothioate linkages are described in WO 97/03211; WO 96/39154; Mata, *Toxicol. Appl. Pharmacol.* 144:189-197, 1997. Other synthetic backbones encompassed by the term include methyl-phosphonate linkages or alternating methylphosphonate and phosphodiester linkages (Strauss-Soukup, *Biochemistry* 36:8692-8698, 1997), and benzylphosphonate linkages (Samstag, *Antisense Nucleic Acid Drug Dev* 6:153-156, 1996). The term nucleic acid is used interchangeably with gene, cDNA, mRNA, oligonucleotide primer, probe and amplification product.

The term "probe" or a "nucleic acid probe", as used herein, is defined to be a collection of one or more nucleic acid fragments whose hybridization to a sample can be detected. The probe may be unlabeled or labeled as described below so that its binding to the target or sample can be detected. The probe is produced from a source of nucleic acids from one or more particular (preselected) portions of the genome, e.g., one or more clones, an isolated whole chromosome or chromosome fragment, or a collection of polymerase chain reaction (PCR) amplification products. Alternatively, the probes of the present invention are synthesized and have sequences corresponding to a source of nucleic acids, e.g., each haplotype of the HLA-B locus. The probes of the present invention correspond to or are produced from nucleic acids found in the regions described herein. The probe or genomic nucleic acid sample may be processed in some manner, e.g., by removal of repetitive nucleic acids or enrichment with unique nucleic acids. The word "sample" may be used herein to refer not only to detected nucleic acids, but also to the detectable nucleic acids in the form in which they are applied to the target. The probe is immobilized on a solid surface (e.g., nitrocellulose, glass, quartz, fused silica slides), as in an array. Techniques capable of producing high density arrays can also be used for this purpose (see, e.g., Johnston, *Curr. Biol.* 8:R171-R174, 1998; Schummer, *Biotechniques* 23:1087-1092, 1997; Kern, *Biotechniques* 23:120-124, 1997; U.S. Pat. No. 5,143,854). One of skill will recognized that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived.

The term "nucleic acid array" as used herein is a plurality of nucleic acid molecules (probes) immobilized on a solid surface (e.g., nitrocellulose, glass, quartz, fused silica slides and the like) to which sample nucleic acids are hybridized. The nucleic acids may contain sequence from specific genes or clones, such as the probes of the invention, as disclosed herein. Other probes optionally contain, for instance, reference sequences. The probes of the arrays may be arranged on the solid surface at different densities. The probe densities will depend upon a number of factors, such as the solid support, the method used to manipulate a sample hybridized on a spot of the array, and the like.

The array components are described in detail below.

Solid Supports

The solid support used in the present invention may be biological, nonbiological, organic, inorganic, or a combination of any of these, existing as gels, sheets, tubing, pads, slices, films, plates, slides, and the like. The solid support is preferably flat, because the size of the genomic DNA to be separated is very large, i.e., about 2 to about 4 Mb), and any method that involves a three-dimensional fluid phase will not ensure specific capture of the genomic DNA to the probe. In some embodiments, the solid support will also be chosen to provide appropriate light-absorbing characteristics. For example, the support can be a polymerized Langmuir Blodgett film, functionalized glass, Si, Ge, GaAs, GaP, $SiO_2$, $SiN_4$, modified silicon, or any one of a variety of gels or polymers such as (poly)tetrafluoroethylene, (poly)vinylidendifluoride, polystyrene, polycarbonate, or combinations thereof. Other suitable solid support materials will be readily apparent to those of skill in the art. Preferably, the surface of the solid support will contain reactive groups, which could be carboxyl, amino, hydroxyl, thiol, or the like. More preferably, the surface will be optically transparent and will have surface S—OH functionalities, such as are found on silica surfaces.

Linking Groups

Attached to the solid support is an optional spacer or linking group. The spacer molecules are typically of sufficient length to permit the oligonucleotide probes in the completed array to interact freely with genomic DNA exposed to the array. The spacer molecules, when present, are typically 6-50 atoms long to provide sufficient exposure for the attached probes. The spacer will typically be comprised of a surface attaching portion and a longer chain portion. The surface attaching portion is that part of the linking group or spacer which is directly attached to the solid support. This portion can be attached to the solid support via carbon-carbon bonds using, for example, supports having (poly)trifluorochloro-ethylene surfaces, or typically, by siloxane bonds (using, for example, glass or silicon oxide as the solid support). Siloxane bonds with the surface of the support are formed in one embodiment via reactions of surface attaching portions bearing trichlorosilyl or trialkoxysilyl groups. The surface attaching groups will also have a site for attachment of the longer chain portion. For example, groups which are suitable for attachment to a longer chain portion would include amines, hydroxyl, thiol, and carboxyl. Typical surface attaching portions include aminoalkylsilanes and hydroxyalkylsilanes. In a particular embodiment, the surface attaching portion of the linking group is either aminopropyltriethoxysilanei or aminopropyl-trimethoxysilane.

The longer chain portion can be any of a variety of molecules which are inert to the subsequent conditions necessary for attaching the oligonucleotide probes, or for hybridization of a sample to the probe array. These longer chain portions will typically be ethylene glycol oligomers containing 2-14 monomer units, diamines, diacids, amino acids, peptides, or combinations thereof. In some embodiments, the longer chain portion is a polynucleotide (e.g., a 15-mer of poly dT). Additionally, for use in synthesis of the probe arrays, the linking group will typically have a protecting group, attached to a functional group (i.e., hydroxyl, amino or carboxylic acid) on the distal or terminal end of the chain portion (opposite the solid support). After deprotection and coupling, the distal end is covalently bound to an oligonucleotide probe (e.g., an HLA-B oligonucleotide probe that hybridizes specifically to one HLA-B haplotype).

HLA Oligonucleotide Probes

Subsequent to haplotype separation of the genomic DNA, linkage analysis can be accomplished. As an example, the haplotyped genomic DNA can be genotyped for HLA-A, C, -DR and/or -DQ genes. An array system for high-resolution genotyping of HLA-A, -B and -C genes has been described by Femandez-Vina et al. (*Tissue Antigens* 45:153-168, 1995), incorporated herein by reference in its entirety). The array is comprised of allele-specific probes (120 for HLA-A, 37 for HLA-B, and 95 for HLA-C) which are informative for all known polymorphisms in exon 2 and exon 3 of the HLA region.

Generally, the key feature of the oligonucleotide array assay is a high redundancy of oligonucleotide probes. In one embodiment of the invention, oligonucleotide probes may be designed to represent at least 80%, preferably at least 90% and more preferably at least 98% of the known polymorphisms in exon 2 and/or exon 3 of HLA-A, -C, -DR and -DQ to determine which alleles are linked with each separated HLA-B haplotype. Known polymorphisms are those that have appeared in the literature or are available from a searchable database of sequences. A panel probes can be designed for polymorphisms in exon 2 and/or for exon 3. All known single allele in either homozygous samples or heterozygous samples could be distinguished from its hybridization pattern with this set of oligonucleotide probes.

The majority of individuals are heterozygous for two different HLA-B alleles. The present method separates a genomic DNA sample into DNA fragments comprising each of these alleles. Sequence polymorphisms or "motifs" can be shared among families of HLA B alleles at a given locus. Therefore, when both HLA-B alleles are separated the polymorphisms linked with each haplotype can be determined. As used herein, the term "allele" refers to a specific version of a nucleotide sequence at a polymorphic genetic locus.

The length of the spacer between the support and the hybridization sequence influences the efficiency of hybridization (Guo et al, *Nuc. Acids Res.* 22:5456 5465, 1994). When large DNA fragments, such as genomic DNA or PCR products, are allowed to hybridize with short oligonucleotide probes immobilized on solid supports, adequate distance between the hybridization sequence and the solid surface may be required in order to achieve the efficient hybridization. This is due to the steric interference between large DNA molecules and the support. A 15 mer dT spacer has been employed in certain instances to provide adequate space between hybridization sequence and the support. Each completed probe contained a 5' amino group for immobilization chemistry, a 20 nucleotide hybridization sequence, and a 15 mer dT spacer between them.

Solution or Solid Phase Methods

Detailed descriptions of the procedures for solution and solid phase synthesis of nucleic acids by phosphite-triester, phosphotriester, and H-phosphonate chemistries are widely available. For example, the solid phase phosphoramidite triester method of Beaucage and Carruthers using an automated synthesizer is described in, e.g., Itakura, U.S. Pat. No. 4,401,796; Carruthers, U.S. Pat. Nos. 4,458,066 and 4,500,707. See also Needham-VanDevanter, *Nucl. Acids Res.* 12:6159-6168, 1984; Beigelman, *Nucl. Acids Res.* 23:3989-3994, 1995; *Oligonucleotide Synthesis: A Practical Approach*, Gait (ed.), IRL Press, Washington D.C., 1984), see Jones, chapt. 2, Atkinson, chapt. 3, and Sproat, chapt. 4; Froehler, *Tetrahedron Lett.* 27:469-472, 1986; Froehler, *Nucl. Acids Res.* 14:5399-5407, 1986. Methods to purify oligonucleotides include native acrylamide gel electrophoresis, anion-exchange HPLC, as described in Pearson, *J. Chrom.* 255:137-149, 1983. The sequence of the synthetic oligonucleotide can be verified using any chemical degradation method, e.g., see Maxam, *Meth. Enzymol.* 65:499-560, 1980; Xiao, *Antisense Nucl. Acid Drug Dev.* 6:247-258, 1996, or for solid-phase chemical degradation procedures, Rosenthal, *Nucleic Acids Symp. Ser.* 18:249-252, 1987.

Solid-Support Based Oligonucleotide Synthesis

An array of oligonucleotide probes at known locations on a single substrate surface can be formed using a variety of techniques known to those skilled in the art of polymer synthesis on solid supports. For example, "light directed" methods (which are one technique in a family of methods known as VLSIPS® methods) are described in U.S. Pat. No. 5,143,854. The light directed methods discussed in the '854 patent involve activating predefined regions of a substrate or solid support and then contacting the substrate with a preselected monomer solution. The predefined regions can be activated with a light source shown through a mask (much in the manner of photolithography techniques used in integrated circuit fabrication). Other regions of the substrate remain inactive because they are blocked by the mask from illumination and remain chemically protected. Thus, a light pattern defines which regions of the substrate react with a given monomer. By repeatedly activating different sets of predefined regions and contacting different monomer solutions with the substrate, a diverse array of polymers is produced on the substrate. Of course, other steps such as washing unreacted monomer solution from the substrate can be used as necessary.

Other useful techniques include mechanical techniques (e.g., flow channel, spotting or pin-based methods). In each of the "flow channel" or "spotting" methods, certain activated regions of the substrate are mechanically separated from other regions when the monomer solutions are delivered to the various reaction sites.

A typical "flow channel" method applied to the compounds and libraries of the present invention can generally be described as follows. Diverse probe sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer B is coupled to second selected regions, some of which may be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form an array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

The "spotting" methods of preparing compounds and libraries of the present invention can be implemented in much the same manner as the flow channel methods. For example, a monomer A can be delivered to and coupled with a first group of reaction regions which have been appropriately activated. Thereafter, a monomer B can be delivered to and reacted with a second group of activated reaction regions. Unlike the flow channel embodiments described above, reactants are delivered by directly depositing (rather than flowing) relatively small quantities of them in selected regions. In some steps, of course, the entire substrate surface can be sprayed or otherwise coated with a solution. In preferred embodiments, a dispenser moves from region to region, depositing only as much monomer as necessary at each stop. Typical dispensers include a micropipette to deliver the monomer solution to the substrate and a robotic system to control the position of the micropipette with respect to the substrate. In other embodiments, the dispenser includes a series of tubes, a manifold, an array of pipettes, or the like so that various reagents can be delivered to the reaction regions simultaneously.

Another method which is useful for the preparation of an array of diverse oligonucleotides on a single substrate involves "pin based synthesis." This method is described in detail in U.S. Pat. No. 5,288,514, incorporated herein by reference. The method utilizes a substrate having a plurality of pins or other extensions. The pins are each inserted simultaneously into individual reagent containers in a tray. In a common embodiment, an array of 96 pins/containers is utilized.

Each tray is filled with a particular reagent for coupling in a particular chemical reaction on an individual pin. Accordingly, the trays will often contain different reagents. Since the chemistry used is such that relatively similar reaction conditions may be utilized to perform each of the reactions, multiple chemical coupling steps can be conducted simultaneously. In the first step of the process, a substrate on which the chemical coupling steps are conducted is provided. The substrate is optionally provided with a spacer (e.g., 15-mer of polydT) having active sites on which the oligonucleotide probes are attached or constructed.

In another aspect, the present invention provides methods of preparing oligonucleotide probe arrays. In this group of embodiments, oligonucleotide probe arrays are prepared by:

(a) contacting a solid support with an aminoalkyltrialkoxysilane in the vapor phase at reduced pressure to form an aminoalkylsilane-derivatized solid support;

(b) contacting the aminoalkylsilane-derivatized solid support with a linking group to covalently attach the linking group to the aminoalkylsilane-derivatized solid support to form a linking group-modified solid support; and (c) attaching a first oligonucleotide probe specific for a first haplotype of HLA-B and a second oligonucleotide probe specific for a second haplotype of HLA-B to the linking group-modified solid support to form the array of covalently-attached oligonucleotide probes.

The solid supports used in this aspect of the invention can be any of those described above which are conveniently derivatized with a vapor phase deposition of an aminoalkyltrialkoxysilane. The use of this vapor phase deposition technique provides a particularly uniform surface for probe assembly and presentation. The aminoalkyltrialkoxysilanes useful in this aspect of the invention are any of those that can be utilized in the vapor phase at temperatures of from about ambient temperature to about 150° C. at pressures of from about 760 mmHg to about 0.1 mmHg. See, for example, WO 00/79006, incorporated herein by reference in its entirety. Typically, the aminoalkyl portion of the silane will be aminopropyl, aminoethyl or aminomethyl. The trialkoxysilane portion can be one in which the alkoxy groups are all the same (e.g., trimethoxysilane, triethoxysilane) or one in which the alkoxy groups are not all alike (e.g., dimethoxyethoxysilane). Accordingly, the aminoalkyltrialkoxysilane will typically be selected from aminopropyltrimethoxysilane, aminopropyltriethoxysilane, aminopropyldiethoxymethoxysilane, aminoethyltrimethoxysilane, and the like. More preferably, the aminoalkyltrialkoxysilane is aminopropyltrimethoxysilane.

As indicated above, a more uniform coating of amino groups on the solid support can be achieved by applying an aminoalkyltrialkoxysilane in the vapor phase, typically at reduced pressure. This can be accomplished by placing the solid support into a vacuum chamber, evacuating the chamber, and introducing the silane. In some embodiments, the vacuum chamber can be heated to facilitate silane vaporization and even coating of the solid support. For example, when aminopropyltrimethoxysilane is used, the pressure will typically be from about 5 to 35 mmHg and the vacuum chamber will be heated to a temperature of from about 60 to about 110° C. After a period of time sufficient for formation of an aminoalkylsilane-derivatized solid support, the support is removed from the vacuum chamber and rinsed to remove any unbound spacer.

The resultant support can then be contacted with a suitable amount of a linking group to covalently attach the linking group to the aminoalkylsilane-derivatized solid support. In some embodiments, the aminoalkylsilane-derivatized solid support will first be treated with a reagent capable of facilitating linking group attachment to the derivatized support. A variety of reagents are useful in this aspect of the invention including diisocyanates, diisothiocyanates, dicarboxylic acids (and their activated esters), and the like. Particular preferred are diisothiocyanates (e.g., 1,4-phenylenediisothiocyanate).

Once the solid support has been suitably derivatized, a linking group is attached to provide a spacing between the oligonucleotide probe and the support which is optimized for interactions between the probes and the sample. As provided above, a variety of linking groups can be used in this aspect of the invention. Preferred groups are those that provide a spacing similar to that provided by a 15-mer polydT spacing group.

Additionally, the linking group will have a reactive portion that is selected to be compatible with the amino group of the aminoalkylsilane-derivatized support, or with the functional group present on the reagent used to facilitate linking group attachment (e.g., the isothiocyanate portion of 1,4-phenylenediisothiocyanate). Accordingly, at the proximal end (that forming an attachment closest to the support), the linking group will have a functional group that is reactive with an amino moiety (e.g., a carboxylic acid, anhydride, isothiocyanate, and the like) or a functional group that is reactive with an isocyanate, isothiocyanate or carboxylic acid moiety (e.g., an amino group, a hydroxyl group or the like).

In a particularly preferred embodiment, the support is derivatized first with aminopropyltrimethoxysilane, followed by attachment of 1,4-phenylenediisothiocyanate, followed by attachment of a 15-mer oligonucleotide, preferably a 15-mer of polydT).

Following construction of the linking group-modified solid support, an oligonucleotide probe specific for a first haplotype of HLA-B and a second oligonucleotide probe specific for a second haplotype of HLA-B are attached to form an array of covalently-attached oligonucleotide probes. The probes are typically 17 to 23 nucleotides in length, with those probes having about 20 nucleotides being particularly preferred. The oligonucleotide probes can be prepared by any conventional methods known to those of skill in the art. Alternatively, the probes can be constructed on the array using the techniques described above (e.g., photolithography, flow channel, inkjet spotting, and the like). In preferred embodiments, the probes are constructed using conventional solution or solid phase chemistry, then attached to that array's solid support component.

In order to determine donor/recipient compatibility in tissue transplants, the practitioner can compare the HLA class I allele and/or HLA class II allele type of both the donor and the recipient. Tools to facilitate such tissue typing and a linkage analysis with a haplotype of an HLA locus are provided herein.

Accordingly, in still another aspect, the present invention provides a method of HLA tissue typing, the method comprising:

(a) separating a genomic DNA sample into a first and a second HLA-B haplotype;

(b) amplifying exons 2 and 3 from the haplotype separated DNA sample using labeled primers and an asymmetric PCR method to form a labeled, single-stranded DNA sample;

(c) contacting the labeled, single-stranded DNA sample under hybridization conditions with an array of HLA Class I oligonucleotide probes prepared by the methods described herein; and (d) detecting a hybridization pattern for the DNA sample and assigning an HLA Class I allele type by analysis of the hybridization pattern with the first and second HLA-B haplotype.

In this method, a genomic DNA sample is obtained from a patient (either a potential donor or recipient) and are separated by their HLA-B haplotype, the exon 2 and exon 3 regions are amplified using labeled primers and an asymmetric PCR method to form a labeled, single-stranded DNA sample. The genomic DNA sample can be obtained from a variety of tissues, depending on the purpose of the diagnostic evaluation. The cell or tissue sample from which the nucleic acid sample is prepared is typically taken from a patient in need of HLA Class I tissue typing for transplant evaluation. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media.

After obtaining a suitable tissue sample, the genomic DNA is isolated by know methods, about 400 ng of genomic DNA is used in a particular embodiment of the present invention. The isolated genomic DNA is contacted with a solid phase having covalently attached thereto an oligonucleotide probe that can specifically separate the haplotypes of an HLA gene, e.g., two oligonucleotide probes that can specifically hybridize each of the two haplotypes of HLA-B. Subsequent to hybridization of the genomic DNA to the oligonucleotide probes and formation of a probe/genomic DNA complex, the excess genomic DNA is eliminated and the haplotype separated genomic DNA is denatured separately from each of the oligonucleotide probes. The haplotype separated genomic DNA the cis/tans association of polymorphisms in other regions of the HLA region can be determined, For example, the nucleic acids of exons 2 and 3 of the HLA-A, —C and exon 2 of the HLA-DRB can be amplified using standard techniques such as PCR (e.g., asymmetric PCR) and labeled primers. The term "labeled primer" as used herein refers to a nucleic acid template for PCR which is attached to a detectable composition, i.e., a label. The detection of the label can be by, e.g., spectroscopic, photochemical, biochemical, immunochemical, physical or chemical means. For example, useful labels include $^{32}P$, $^{35}S$, $^{3}H$, $^{14}C$, $^{125}I$, $^{131}I$; fluorescent dyes (e.g., a dipyrrometheneboron difluoride fluorophore (BDY), FITC, rhodamine, lanthamide phosphors, Texas red), electron-dense reagents (e.g., gold), enzymes, e.g., as commonly used in an ELISA (e.g., horseradish peroxidase, β-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. The label can be directly incorporated into the nucleic acid to be detected. Additionally, the label can be attached by spacer arms of various lengths to reduce potential steric hindrance or impact on other useful or desired properties. See, e.g., Mansfield, *Mol Cell Probes* 9:145-156, 1995.

The terms "hybridizing specifically to" and "specific hybridization" and "selectively hybridize to," as used herein refer to the binding, duplexing, or hybridizing of a nucleic acid molecule preferentially to a particular nucleotide sequence under stringent conditions. The term "stringent conditions" or "hybridization conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. An extensive guide to the hybridization of nucleic acids is found in, e.g., Tijssen, *Laboratory Techniques in Biochemistry and Molecular Biology—Hybridization with Nucleic Acid Probes* part I, chapt 2, "Overview of principles of hybridization and the strategy of nucleic acid probe assays," Elsevier, NY, 1993 ("Tijssen"). Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on an array or on a filter in a Southern or northern blot is 42° C. using standard hybridization solutions (see, e.g., Sambrook and detailed discussion, below), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook, *Molecular Cloning: A Laboratory Manual* (2nd ed.) Vol. 1-3, Cold Spring Harbor Laboratory, Cold Spring Harbor Press, NY, 1989 ("Sambrook") for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes. Within one embodiment of the invention, separation of HLA-B haplotypes was accomplished by hybridization of the genomic DNA fragments with the oligonucleotide probes at room temperature for three hours. The excess genomic DNA washed away with a buffer wash and the haplotype separated genomic DNA removed from each HLA-B haplotype specific probe by denaturing the genomic DNA/probe complex at 50° C. in double distilled water. The haplotype separated genomic DNA could then be further characterized and typed for linkage of HLA-A, —C, DR and DQ alleles by hybridization with oligonucleotide arrays by, for example, hybridization at 37° C. for two hours in 5×SSPE, 0.5% SDS was followed by two fifteen minute washes at stringent conditions in 20×SSPE, 0.2% SDS at 30° C.

In an array format a large number of different hybridization reactions can be run essentially "in parallel." This provides rapid, essentially simultaneous, evaluation of a large number of loci. Methods of performing hybridization reactions in array based formats are also described in, e.g., Pastinen, *Genome Res.* 7:606-614, 1997; Jackson, *Nature Biotechnology* 14:1685, 1996; Chee, *Science* 274:610, 1995; and WO 96/17958.

To optimize a given assay format, one of skill can determine sensitivity of label (e.g., fluorescence) detection for different combinations of membrane type, fluorochrome, excitation and emission bands, spot size and the like. Low fluorescence background membranes can be used (see, e.g., Chu, Electrophoresis 13:105-114, 1992). The sensitivity for detection of spots ("target elements") of various diameters on the candidate membranes can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., membranes, glass, fused silica) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

Arrays on solid surface substrates with much lower fluorescence than membranes, such as glass, quartz, or small beads, can achieve much better sensitivity. Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques (described above). Nucleic acids can be conveniently coupled to glass using commercially available reagents. For instance, materials for preparation of silanized glass with a number of functional groups are commercially available or can be prepared using standard techniques (see, e.g., Gait, *Oligonucleotide Synthesis: A Practical Approach*, IRL Press, Wash., D.C., 1984). Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using, e.g., protein A following standard protocols (see, e.g., Smith, *Science* 258:1122-1126, 1992). Biotin or digoxigenin end-labeled nucleic acids can be prepared according to standard techniques. Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In one particularly preferred embodiment, oligonucleotide probe specific for each haplotype of HLA-B are spotted onto a surface (e.g., a glass or quartz surface). The nucleic acid is dissolved in a mixture of dimethylsulfoxide (DMSO) and spotted onto amino-silane coated glass slides. Small capillaries tubes can be used to "spot" the probe mixture.

In related aspects, the present invention provides a method of HLA tissue typing, the method comprising:

(a) contacting under hybridization conditions a genomic DNA sample with an HLA-B probe array that is constructed to separate the two HLA-B haplotypes;

(b) separating the genomic DNA sample from each HLA-B haplotype specific probe;

(c) selectively amplifying the HLA regions in a genomic sample using asymmetric PCR and labeled primers to form a labeled, single-stranded DNA sample;

(d) contacting under hybridization conditions the labeled, single-stranded DNA sample with an HLA microarray prepared by any of the methods described herein; and (e) detecting a hybridization pattern for the DNA sample and assigning an HLA allele type by analysis of the hybridization pattern.

In another related aspect, the present invention provides a method for determining the HLA-A typing linked with a haplotype of HLA-B, the method comprising:

(a) contacting under hybridization conditions a genomic DNA sample with an HLA-B probe array that is constructed to separate the two HLA-B haplotypes;

(b) separating the genomic DNA sample from each HLA-B haplotype specific probe;

(c) amplifying exons 2 and 3 from the haplotype separated genomic DNA sample using labeled primers and an asymmetric PCR method to form a labeled, single-stranded DNA sample;

(d) contacting under hybridization conditions, the labeled, single-stranded DNA sample with any HLA-A microarray; and (e) detecting a hybridization pattern for the DNA sample and assigning an HLA-A allele type linked to each HLA-B haplotype by analysis of the hybridization pattern.

In another related aspect, the present invention provides a method of HLA-C tissue typing, the method comprising:

(a) contacting under hybridization conditions a genomic DNA sample with an HLA-B probe array that is constructed to separate the two HLA-B haplotypes;

(b) separating the genomic DNA sample from each HLA-B haplotype specific probe;

(c) amplifying exons 2 and 3 from a genomic sample of tissue using labeled primers and an asymmetric PCR method to form a labeled, single-stranded DNA sample;

(d) contacting under hybridization conditions, the labeled, single-stranded DNA sample with any HLA-C microarray; and (e) detecting a hybridization pattern for the DNA sample and assigning an HLA-C allele type linked with each haplotype of HLA-B by analysis of the hybridization pattern.

EXAMPLES

The following examples are offered to illustrate, but not to limit the scope of the claimed invention.

Example 1

This example illustrates the separation of large genomic DNA fragments based on separation of the HLA-B haplotypes by contacting a genomic DNA sample with an oligonucleotide array comprising probes designed to hybridize specifically with each of the two HLA-B haplotypes immobilized on a flat solid phase surface.

The key feature of the separation of the large genomic DNA fragment is that a flat, solid-phase surface is used that provides a sufficient concentration of probe on the solid-phase surface to ensure capture. Any method that involves a three-dimensional fluid phase will not ensure specific capture. Further, the separation of HLA-B haplotypes is based on the discrimination of differences between the primary nucleotide sequences of the haplotypes and not on size, as the two haplotypes have identical or similar basepair lengths. The HLA probes are designed so that they only capture one of the two haplotypes based on known HLA polymorphisms. The oligonucleotide probes used in the manufacture of oligonucleotide arrays contain a 5' amino group for immobilization chemistry. Concentrations of all oligonucleotides were determined by UV spectrophotometry at 260 nm. Probes were immobilized on solid supports and hybridized with genomic DNA. Subsequent to separation of the large genomic DNA fragments, the typing of HLA-A, -B, -C, -DR, and -DQ and their linkage to each HLA-B haplotype can be determined by known methods such as those disclosed in WO 00/79006, incorporated herein by reference in its entirety for all purposes.

Oligonucleotide probes were selected to encode a sequence of nucleotides that unequivocally distinguish the two HLA-B alleles in the samples. HLA-B oligonucleotide arrays were constructed on treated microscopic slides by attaching pre-synthesized oligonucleotide probes. The two probes were arrayed onto the slide to allow separate manipulation of each spot. Genomic DNA was allowed to hybridize to the probes; the DNA from one haplotype hybridizing only to the probe that shared complementarity in sequence, and that of the second haplotype hybridizing to the second probe. Excess genomic DNA was eliminated with a buffer wash and the bound genomic DNA released from each of the probes and collected separately. At this point in the assay the two HLA-B haplotypes had been separated. For samples with two identical HLA-B alleles (i.e., homozygous), the haplotypes were separated on the basis of the HLA-A polymorphisms.

Briefly, oligonucleotide probes were diluted from a starting concentration of 1 nM/µl to a concentration of 250 pmol/µl by adding equal amounts of probe to DMSO, applied to glass slides by using a Molecular Dynamic (Sunnyvale, Calif.) spotter system and immobilized on glass supports by covalent binding.

New glass slides were washed once in hydrogen peroxide in a slide dish for 15 min at room temperature, washed two times with distilled water, five minutes per wash, then washed in acetone for 5 min, and air dried. The cleaned slides were placed in a vacuum chamber with 700 microliters 3-aminopropyltrimethoxysilane (Aldrich Chemical, Milwaukee, Wis.) and the vacuum chamber was kept at 120° C. and 30 ppm Hg pressure for 3 hours. The slides were cooled in the vacuum oven for 1 hr, then taken from the vacuum chamber and washed 4 times with acetone, five minutes per wash. The slides were then treated for 2 hours with a thiocyanate solution (0.4 g 1,4 phenylene diisothiocyanate (Aldrich) in 180 ml N,N-dimethylformamide, 20 ml pyridine), let stand for 3 hr in the dark, and then washed alternately with methanol and acetone for 4 washes, 5 minutes per wash. The activated glass slides may be stored indefinitely at 4° C. in a vacuum dessicator containing anhydrous calcium chloride without discernible loss of activity.

The HLA-B oligonucleotide probes were deposited 3 times (3 µl each time) onto pre-marked slides into the center of each spot. Slides spotted with oligonucleotide probes were then baked at 90° C. for 3 hr, removed, washed once with 1% NH$_4$OH, four times with water, and air dried at room temperature. The slides were now ready for hybridization experiments. It is not recommended that the slides be employed multiple times, as rapidly increased background is observed.

The oligonucleotide probes were linked to the glass surface by covalent bonding (Guo et al., *Nucl. Acids Res.* 22:5456-5465, 1994). The immobilization chemistry included three steps: a) reaction of the pre cleaned glass slides with aminopropyltrimeth-oxylsilane vapor in vacuum chamber to generate an amino derivatized surface; b) coupling of the amino group on the glass surface with excess p-phenylene diisothiocyanate to convert the amino groups to amino reactive phenylisothiocyanate groups; and c) coupling of 5' amino modified oligonucleotide probes to these amino reactive groups to yield the surface bound oligonucleotide.

Efficient and stable oligonucleotide coupling was achieved using this immobilization chemistry. Oligonucleotide arrays could be washed with water and stored at, room temperature for a considerable period without any observable loss of oligonucleotides. The surface density of each oligonucleotide probe could be easily adjusted by changing the concentration of the oligonucleotide solution during the application step period. Prior to using the slides in the genomic DNA hybridization-splitting haplotype method the slides were pre-treated with a Salmon DNA cocktail. Briefly, 10 µl of Salmon sperm DNA cocktail (2 µl 1:10 salmon sperm DNA, 2.5 µl 20×SSPE, 5.5 µl ddH$_2$O times the number of spots to be treated) was deposited onto each probe spot. The slide was placed into a hybridization chamber for 2 hr at room temperature. After hybridization the slides were removed and washed twice with SSPE at 5 min per wash. The slides were allowed to air dry until the SSPE was gone.

Example 2

This example illustrates the separation of the HLA-B haplotypes.

Human genomic DNA samples encoding various HLA-B genotypes were studied. 20 µl of a selected genomic DNA sample (100 ng/µl) were boiled for 2 min and immediately dropped into ice and cooled for about 2 to 5 min. The sample was removed from the ice and 5 µl of 20×SSPE was added with gentle pipetting to mix. A drop of 4 µl of the DNA/SSPE solution was placed into the center of each spot/probe, which had been previously marked with a circle on the glass slide. The slide was incubated in at room temperature in the hybridization chamber for 3 hr in the presence of double distilled H$_2$O (ddH$_2$O). After the incubation period, the slide was removed and washed twice with 200 ml of 2×SSPE for 5 min. The slides were removed from the wash and allowed to air dry until the SSPE was gone. The slide was replaced in the hybridization chamber at 50° C. and denatured by the addition of 10 µl of 50° C. ddH$_2$O to each spot. The denaturation was allowed to proceed for 1 min, and the denatured DNA and ddH$_2$O removed from the slide with a pipette and put into tubes according to the labeled spot. If the samples were arrayed in duplicate, both samples were placed into the same tube to increase the yield. The integrity of the extracted DNA can be verified by agarose gel electrophoresis and the concentration of captured DNA measured by UV spectrometry. The genomic DNA can now be typed for the remaining HLA genes and linkage with each HLA-B haplotype determined.

A two step PCR strategy was used to perform PCR on each HLA-B haplotype for exons 2 and 3 of HLA-A, —C, and exon 2 of HLA-DRB. In the first step, genomic DNA was used as the template to regions of HLA-A, -C, and -DBR, as identified below, by PCR using two primers to generate double stranded PCR products; in the second step, the PCR product obtained from the first amplification was amplified by PCR with only one primer, so that only one DNA strand would be amplified in this step. The single stranded product generated in this approach had very high hybridization efficiency when applied to the oligonucleotide array.

Exon 2 of the HLA-A gene was amplified by two step asymmetric PCR. In the first step, the PCR primers were primer AF1/AF2-2 located at intron 1, positions 45-27 (5' GCCTCTGTCGGGGAGAAGCA 3'; SEQ ID NO: 1) and primer AR2A/AR2B-2, located at exon 2, position 251-234 (5' GTAGCCGGCAGCAGGCGGATCCCG 3'; SEQ ID NO: 2). The 47.5 microliter amplification reaction contained 37.1 µl of ddH$_2$O, 5 µl 10×PCR buffer with MgCl$_2$ (Lifecodes), 2.5 µl of haplotype split genomic DNA, 100 µmol of each primer (0.5 µl each), 10 mM dNTP mix (Boehringer Mannheim), and 0.4 µl of Taq DNA polymerase (Fastart®, Roche). The sample was incubated at 95° C. for 4 min prior to amplification, where the reaction was performed in a Perkin Elmer Cetus 9600 thermal cycler using 40 cycles of the following profile: 95° C. for 30 sec, 60° C. for 30 sec and 72° C. for 1 minute. The reaction was held at 4° C. until the PCR mixture was purified using a QIAGEN PCR purification kit (QIAGEN Inc.) to remove the excess primers. 5 µl of the amplified product was run on a 1% agarose gel to check the size of the amplified product which should be approximately 351 bp.

In the second step, the PCR primer employed was a 5' BDY (dipyrrometheneboron difluoride fluorophore) labeled AF1/AF2-2 primer (SEQ ID NO: 1). The 50 µl amplification reaction contained 3 µl of purified double stranded PCR template, 30.0 µl of ddH$_2$O, 10 µl 10×PCR buffer with MgCl$_2$ (Lifecodes), 4 µl 10 mM dNTP mix (Boehringer Mannheim), 2.5 µl of 10 µmol AF1/AF2-2 primer and 0.5 µl Taq DNA polymerase (Amplitaq® Polymerase). The PCR was performed subsequent to incubation for 3 min at 96° C. in 30 cycles using the following profile: 96° C. for 30 seconds, 64° C. for 30 sec and 72° C. for 1 min. 10 µl of the amplified product was run on a 2% agarose gel to check the size and quantity of the amplified product.

Amplification of exon 3 of HLA-A was accomplished using primer AF1-3/AF2-3 (5' AGTTTAGGC-CAAAAATCTCGCC; SEQ ID NO: 3), located at intron 2, position 200-180, and primer AR-3 (5' GTGGCCCCTC-CTACCCGTG 3'; SEQ ID NO: 4), located at intron 3, position 14 to exon 3, position 272. The 47.5 µl ampification reaction contained 37.1 µl of ddH$_2$O, 5 µl 10×PCR buffer with MgCl$_2$ (Lifecodes), 2.5 µl of haplotype split genomic DNA, 100 µmol of each primer (0.5 µl each), 10 mM dNTP mix (Boehringer Mannheim), and 0.4 µl of Taq DNA polymerase (Fastart®, Roche). Subseqeunt to a 4 min incubation at 95° C., the amplification reaction was performed in a Perkin Elmer Cetus 9600 thermal cycler using 40 cycles of the following profile: 95° C. for 30 sec, 60° C. for 30 sec and 72° C. for 1 minute. The reaction was held at 4° C. until the PCR mixture was purified using a QIAGEN PCR purification kit (QIAGEN Inc.) to remove the excess primers. 5 µl of the amplified product was run on a 1% agarose gel to check the size of the amplified product which should be approximately 371 bp.

In the second step, the PCR primer employed was BDY (a dipyrrometheneboron difluoride fluorophore) labeled primer ARO-3 (5' BDY-TCTCCAGGTATCTGCGGAGC 3' SEQ ID NO: 5), located at exon 3, position 249-230. The 50 µl amplification reaction contained 3 µl of purified double stranded PCR template, 30.0 µl ddH₂O, 10 µl 10×PCR buffer with MgCl₂ (Lifecodes), 4 µl 10 mM dNTP mix (Boehringer Mannheim), 2.5 µl of 10 pmol BDY-labeled-ARO-3 primer and 0.5 µl Taq DNA polymerase (Amplitaq® Polymerase). The PCR was performed subsequent to incubation for 3 min at 96° C. in 30 cycles using the following profile: 96° C. for 30 seconds, 64° C. for 30 sec and 72° C. for 1 min. 10 µl of the amplified product was run on a 2% agarose gel to check the size and quantity of the amplified product.

Amplification of exon 2 of HLA-C was accomplished using $C_{1-2}$ primer (5' GACCCGGGGAGCCGCGCA; SEQ ID NO: 6), located at intron 1, position 88-71, and the primer CRO-2 (5'CTCTGGTTGTAGTAGCCGCG 3'; SEQ ID NO: 7), located at exon 2, position 262-234. The 47.5 µl ampification reaction contained 37.1 µl of ddH₂O, 5 µl 10×PCR buffer with MgCl₂ (Lifecodes), 2.5 µl of haplotype split genomic DNA, 100 µmol of each primer (0.5 µl each), 10 mM dNTP mix (Boehringer Mannheim), and 0.4 µl of Taq DNA polymerase (Fastarti®, Roche). Subsequent to an incubation at 95° C. for 4 min, the amplification reaction was performed in a Perkin Elmer Cetus 9600 thermal cycler using 40 cycles of the following profile: 95° C. for 30 sec, 60° C. for 30 sec and 72° C. for 1 minute. The reaction was held at 4° C. until the PCR mixture was purified using a QIAGEN PCR purification kit (QIAGEN Inc.) to remove the excess primers. 5 µl of the amplified product was run on a 1% agarose gel to check the size of the amplified product which should be approximately 318 bp.

In the second step, the PCR primer employed was BDY (a dipyrrometheneboron difluoride fluorophore) labeled primer CRO-2 (SEQ ID NO: 7), located at exon 2, position 262-234. The 50 µl amplification reaction contained 3 µl of purified double stranded PCR template, 30.0 µl of ddH₂O, 10 µl 10×PCR buffer with MgCl₂ (Lifecodes), 4 µl 10 mM dNTP mix (Boehringer Mannheim), 2.5 µl of 10 µmol BDY-labeled-CRO-2 primer and 0.5 µl taq DNA polymerase (Amplitaq® Polymerase). The PCR was performed subsequent to incubation for 3 min at 96° C. in 30 cycles using the following profile: 96° C. for 30 seconds, 64° C. for 30 sec and 72° C. for 1 min. 10 µl of the amplified product was run on a 2% agarose gel to check the size and quantity of the amplified product.

Amplification of exon 3 of HLA-C was accomplished using primer CFO3-3 (5'CCTTTACCCGGTTTCATTTTC; SEQ ID NO: 8), located at intron 2, position 179-159, and primer C2-3 (5' ATTTTCCTCCCCTCCTCGTG 3'; SEQ ID NO: 9), located at intron 3, position 90-71. The 47.5 µl ampification reaction contained 37.1 µl of ddH₂O, 5 µl 10×PCR buffer with MgCl₂ (Lifecodes), 2.5 µl of haplotype split genomic DNA, 100 pmol of each primer (0.5 µl each), 10 mM dNTP mix (Boehringer Mannheim), and 0.4 µl of Taq DNA polymerase (Fastart®, Roche). Subsequent to a 4 min incubation at 95° C., the amplification reaction was performed in a Perkin Elmer Cetus 9600 thermal cycler using 40 cycles of the following profile: 95° C. for 30 sec, 60° C. for 30 sec and 72° C. for 1 minute. The reaction was held at 4° C. until the PCR mixture was purified using a QIAGEN PCR purification kit (QIAGEN Inc.) to remove the excess primers. 5 µl of the amplified product was run on a 1% agarose gel to check the size of the amplified product which should be approximately 468 bp.

In the second step, the PCR primer employed was a BDY (dipyrrometheneboron difluoride fluorophore) labeled primer $C_{2-3}$ (SEQ ID NO: 9), located at intron 3, position 90-71. The 50 µl amplification reaction contained 3 µl of purified double stranded PCR template, 30.0 µl of dd H₂O, 10 µl 10×PCR buffer with MgCl₂ (Lifecodes), 4 µl 10 mM dNTP mix (Boehringer Mannheim), 2.5 µl of 10 µmol BDY-labeled-ARO-3 primer (SEQ ID NO: 5) and 0.5 µl Taq DNA polymerase (Amplitaq® Polymerase). The PCR was performed subsequent to incubation for 3 min at 96° C. in 30 cycles using the following profile: 96° C. for 30 seconds, 62° C. for 30 sec and 72° C. for 1 min. 10 µl of the amplified product was run on a 2% agarose gel to check the size and quantity of the amplified product.

Amplification of exon 3 of HLA-DRB was accomplished using primer DRB-GH46 (5'CCGGATCCTTCGTGTC-CCCACAGCACG; SEQ ID NO: 10), located at position 4 OF EXON 2, and primer 2DRBAMP-B (5'CCGCTGCACT-GTGAAGCTCT 3'; SEQ ID NO: 11), located at position 279-260 of exon 2. The 47.5 µl amplification reaction contained 37.1 µl of ddH₂O, 5 µl 10×PCR buffer with MgCl₂ (Lifecodes), 2.5 µl of haplotype split genomic DNA, 100 pmol of each primer (0.5 µl each), 10 mM dNTP mix (Boehringer Mannheim), and 0.4 µl of Taq DNA polymerase (Fastart®, Roche). Subsequent to a 4 min incubation at 95° C., the amplification reaction was performed in a Perkin Elmer Cetus 9600 thermal cycler using 40 cycles of the following profile: 95° C. for 30 sec, 60° C. for 30 sec and 72° C. for 1 minute. The reaction was held at 4° C. until the PCR mixture was purified using a QIAGEN PCR purification kit (QIAGEN Inc.) to remove the excess primers. 5 µl of the amplified product was run on a 1% agarose gel to check the size of the amplified product which should be approximately 200 bp.

In the second step, the PCR primer employed was a BDY labeled primer 2DRBAMP-B (SEQ ID NO: 11), located at position 4 of exon 2. The 50 µl amplification reaction contained 3 µl of purified double stranded PCR template, 30.0 µl of double distilled H₂O, 10 µl 10×PCR buffer with MgCl₂ (Lifecodes), 4 µl 10 mM dNTP mix (Boehringer Mannheim), 2.5 µl of 10 µmol BDY-labeled-ARO-3 primer and 0.5 µl Taq DNA polymerase (Amplitaq®Polymerase). The PCR was performed subsequent to incubation for 3 min at 96° C. in 30 cycles using the following profile: 96° C. for 30 seconds, 62° C. for 30 sec and 72° C. for 1 min. 10 µl of the amplified product was run on a 2% agarose gel to check the size and quantity of the amplified product.

Example 3

The example illustrates the hybridization and typing of HLA-A, —C and -DRB of haplotype split DNA samples to the HLA-A, —C and -DRB microarrays.

Oligonucleotide arrays can be constructed as follows. Array slides can be prepared as described above, briefly new glass slides were washed once in hydrogen peroxide in a slide dish for 15 min at room temperature, washed two times with ddH₂O, five minutes per wash, then washed in acetone for 5 min, and air dried. The cleaned slides were placed in a vacuum chamber with 700 microliters 3-aminopropyltri-methoxysilane (Aldrich Chemical, Milwaukee, Wis.) and the vacuum chamber was kept at 120° C. and 30 ppm Hg pressure for 3 hours. The slides were cooled in the vacuum oven for 1 hr, then taken from the vacuum chamber and washed 4 times with acetone, five minutes per wash. The slides were then treated for 2 hours with a thiocyanate solution (0.4 g 1,4 phenylene diisothiocyanate (Aldrich) in 180 ml N,N-dimethylformamide, 20 ml pyridine), let stand for 3 hr in the dark, and then washed alternately with methanol and acetone for 4 washes, 5 minutes per wash. The activated glass slides may be stored indefinitely at 4° C. in a vacuum dessicator containing anhydrous calcium chloride without discernible loss of activity.

Oligonucleotide probes, for example, from the HLA-A, -C, -DR and -DQ regions can be produced. The oligonucleotide probes are placed in 96 well plates with DMSO in a Perkin Elmer Spot Array 24 Spotter along with the prepared slides. Oligonucleotide probes were spotted twice at a predetermined location on the slide and allowed to sit at room temperature overnight at 55% humidity, before baking in an oven at 90° C. for 3 hr. The slides were removed from the oven and washed once with 1:100 $NH_4OH$ and then rinsed 4 times with $ddH_2O$ on an orbital shaker.

Single stranded HLA-A, -B, -C, and -DRB oligonucleotides generated by asymmetric PCR using a fluorescently labeled primer as described above, were diluted using hybridization buffer. For hybridization oligonucleotide arrays, fifty microliter solution of the single stranded BDY labeled PCR product was reduced to 30 µl in a SPEED VAC, and 6 µl of 20×SSPE, and 1.5 µl of 10% SDS was added. This mixture was applied to the array slide and covered with a cover glass, and incubated at 30° C. for 3 hours. The glass slide was then washed twice with preheated 37° C. washing buffer (0.2×SSPE, 0.2% SDS, $ddH_2O$) at 37° C., 15 minutes each. After hybridization and washing process, fifty microliters of washing solution (2×SSPE, 0.2% SDS) was applied to the glass slide, and the slide was covered with a cover glass. This provides an aqueous environment for the fluorescence scanning. Positive hybridization results were detected by fluorescence scanning of the slide using a Perkin Elmer Scan Array Scanner.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for separating large fragments of genomic DNA by haplotype, comprising:
   (a) providing a flat solid surface comprising covalently bound oligonucleotide probes having a nucleotide sequence complementary to each haplotype of an HLA allele;
   (b) contacting the oligonucleotide probes with a sample of genomic DNA under conditions conducive to specific hybridization of the genomic DNA to the oligonucleotide probes to form a genomic DNA/oligonucleotide complex;
   (c) removing excess genomic DNA;
   (d) denaturing the genomic DNA/oligonucleotide complex; and
   (e) separately collecting the genomic DNA corresponding to each haplotype;
   thereby separating the large fragments of genomic DNA by haplotype.

2. The method according to claim 1, wherein the HLA allele is an HLA-B allele.

3. The method according to claim 1, wherein the oligonucleotide probes are about 20 to about 40 bases in length.

4. The method according to claim 1, wherein the oligonucleotide probes are spaced to allow independent manipulation of the genomic DNA hybridized to each probe.

5. The method of claim 1, wherein the hybridization is carried out at a temperature of less than 30 degrees Celsius for 3 hours or more.

6. The method according to claim 1, wherein said large fragments of genomic DNA have a length of 2 megabases (Mb) to 4 megabases (Mb).

7. The method according to claim 1, wherein the solid surface comprises glass.

8. The method according to claim 1, wherein the solid surface comprises a glass slide.

9. The method according to claim 1, wherein the solid surface has been derivatized with a vapor phase deposition of an aminoalkyltrialkoxysilane.

10. The method according to claim 9, wherein the aminoaklyltrialkoxysilane is 3-aminopropyltrimethoxylsilane.

11. The method according to claim 1, wherein the HLA allele is an HLA-A allele.

12. The method according to claim 1, wherein the HLA allele is selected from the group consisting of an HLA-C allele, an HLA-DR allele, and HLA-DQ allele, and an HLA-DP allele.

13. The method according to claim 1, wherein said covalently bound oligonucleotide probes further comprise a linking group, and wherein said linking group is sufficient to provide optimum binding of said fragments of genomic DNA to said oligonucleotide probes.

14. The method according to claim 1, wherein said removing step is carried out by washing with buffer.

15. The method according to claim 14, wherein said linking group is a poly dT spacer.

* * * * *

UNITED STATES PATENT AND TRADEMARK OFFICE
CERTIFICATE OF CORRECTION

PATENT NO. : 7,300,755 B1
APPLICATION NO. : 10/843985
DATED : November 27, 2007
INVENTOR(S) : Petersdorf et al.

Page 1 of 1

It is certified that error appears in the above-identified patent and that said Letters Patent is hereby corrected as shown below:

Column 1, Line 16: Please correct by adding --CA100019,-- before "CA72978 and".

Signed and Sealed this

Thirteenth Day of July, 2010

David J. Kappos
*Director of the United States Patent and Trademark Office*

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: PCR primer AF1/AF2-2

<400> SEQUENCE: 1
gcctctgtcg gggagaagca                                             20

<210> SEQ ID NO 2
<211> LENGTH: 24
<212> TYPE: DNA
<213> ORGANISM: Artificial Sequence
<220> FEATURE:
<223> OTHER INFORMATION: PCR primer AR2A/AR2B-2

<400> SEQUENCE: 2
gtagccggca gcaggcggat cccg                                        24

<210> SEQ ID NO 3
<211> LENGTH: 22
<212> TYPE: DNA
<213> ORGANISM: Artificial Sequence
<220> FEATURE:
<223> OTHER INFORMATION: PCR primer AF1-3/AF2-3

<400> SEQUENCE: 3
agtttaggcc aaaaatctcg cc                                          22

<210> SEQ ID NO 4
<211> LENGTH: 19
<212> TYPE: DNA
<213> ORGANISM: Artificial Sequence
<220> FEATURE:
<223> OTHER INFORMATION: PCR primer AR-3

<400> SEQUENCE: 4 gtggccctc ctacccgtg                                               19

<210> SEQ ID NO 5
<211> LENGTH: 20

```
<212> TYPE: DNA
<213> ORGANISM: Artificial Sequence
<220> FEATURE:
<223> OTHER INFORMATION: PCR primer ARO-3

<400> SEQUENCE: 5
tctccaggta tctgcggagc                                               20

<210> SEQ ID NO 6
<211> LENGTH: 18
<212> TYPE: DNA
<213> ORGANISM: Artificial Sequence
<220> FEATURE:
<223> OTHER INFORMATION: PCR primer C1-2

<400> SEQUENCE: 6
gacccgggga gccgcgca                                                 18

<210> SEQ ID NO 7
<211> LENGTH: 20
<212> TYPE: DNA
<213> ORGANISM: Artificial Sequence
<220> FEATURE:
<223> OTHER INFORMATION: PCR primer CRO-2

<400> SEQUENCE: 7
ctctggttgt agtagccgcg                                               20

<210> SEQ ID NO 8
<211> LENGTH: 21
<212> TYPE: DNA
<213> ORGANISM: Artificial Sequence
<220> FEATURE:
<223> OTHER INFORMATION: PCR primer CFO3-3

<400> SEQUENCE: 8
cctttacccg gtttcatttt c                                             21

<210> SEQ ID NO 9
<211> LENGTH: 20
<212> TYPE: DNA
<213> ORGANISM: Artificial Sequence
<220> FEATURE:
<223> OTHER INFORMATION: PCR primer C2-3

<400> SEQUENCE: 9
attttcctcc cctcctcgtg                                               20

<210> SEQ ID NO 10
<211> LENGTH: 27
<212> TYPE: DNA
<213> ORGANISM: Artificial Sequence
<220> FEATURE:
<223> OTHER INFORMATION: PCR primer DRB-GH46

<400> SEQUENCE: 10
ccggatcctt cgtgtcccca cagcacg                                       27

<210> SEQ ID NO 11
<211> LENGTH: 20
<212> TYPE: DNA
<213> ORGANISM: Artificial Sequence
<220> FEATURE:
<223> OTHER INFORMATION: PCR primer 2DRBAMP-B
```

-continued

<400> SEQUENCE: 11
ccgctgcact gtgaagctct                                                                 20